United States Patent [19]

Lin

[11] Patent Number: 5,686,640
[45] Date of Patent: Nov. 11, 1997

[54] PRODUCTION AND UTILIZATION OF TRI-(BETA-BRANCHED ALKYL) ALUMINUM COMPOUNDS

[75] Inventor: Kaung-Far Lin, Baton Rouge, La.

[73] Assignee: Albemarle Corporation, Richmond, Va.

[21] Appl. No.: 708,019

[22] Filed: Aug. 30, 1996

[51] Int. Cl.$^6$ .................................................. C07F 5/06
[52] U.S. Cl. .................................................. 556/190
[58] Field of Search .................................................. 556/190

[56] References Cited

U.S. PATENT DOCUMENTS

| | | | |
|---|---|---|---|
| 3,282,974 | 11/1966 | Bruno et al. | 260/448 |
| 3,389,161 | 6/1968 | Kottong et al. | 260/448 |
| 4,960,878 | 10/1990 | Crapo et al. | 556/179 |
| 4,973,788 | 11/1990 | Lin et al. | 585/511 |
| 5,041,584 | 8/1991 | Crapo et al. | 556/179 |
| 5,086,024 | 2/1992 | Crapo et al. | 502/117 |
| 5,144,053 | 9/1992 | Allen et al. | 556/190 |
| 5,354,433 | 10/1994 | Granneman et al. | 556/190 X |
| 5,498,735 | 3/1996 | Takeuchi et al. | 556/190 X |
| 5,597,937 | 1/1997 | Samsel | 556/190 |

OTHER PUBLICATIONS

Ziegler, et al., *Justus Liebigs Ann. Chem.*, vol. 629, pp. 53–89 (1960) (57–page English translation attached).
*Chemical Abstracts*, 52:1203–04, 1960, 52:7351–52, 1961; 54:24355–56, 1961.

*The Use of Aluminum Alkyls in Organic Synthesis*, Ethyl Corporation, pp. 1–75 (2nd Printing, Mar., 1977).

*Primary Examiner*—Paul F. Shaver
*Attorney, Agent, or Firm*—Philip M. Pippenger

[57] ABSTRACT

Processes are described for the production and use of tri-(beta-branched alkyl)aluminum compounds. In a preferred embodiment, a process of this invention involves dimerizing one or more vinylolefin monomers with an alkyl aluminum catalyst to form a first product mixture comprising at least vinylolefin monomer, trialkylaluminum in which each alkyl group has the same number of carbon atoms and skeletal structure as said vinylolefin monomer, and vinylidene olefin. The vinylolefin monomer is then removed while concurrently the trialkylaluminum and vinylidene olefin are converted to tri-(beta-branched alkyl)aluminum by reactive distillation. Reactive distillation effects a shift of the chemical equilibrium away from the trialkylaluminum compound and toward the production of tri-(beta-branched alkyl)aluminum. compound. The tri-(beta-branched alkyl) aluminum compound may then be purified by a subsequent distillation, or similarly purified and recycled back into the process as the alkyl aluminum catalyst used in forming the first product mixture. The described processes constitute highly efficient economical processes which may be carried out in a single reactor, if desired, for the high-yield production and use of such compounds.

26 Claims, No Drawings

PRODUCTION AND UTILIZATION OF TRI-(BETA-BRANCHED ALKYL) ALUMINUM COMPOUNDS

TECHNICAL FIELD

This invention pertains to novel process technology involving the production and utilization of tri-(beta-branched alkyl)aluminum compounds.

Glossary

As used herein the following terms, whether singular or plural and whether capitalized or not, have the following meanings:

"Vinylolefin" is an olefin having the structure $(R^1)HC=CH_2$, where $R^1$ is an alkyl group.

"Vinylidene Olefin" is an olefin having the structure $(R^1)(R^2)C=CH_2$ in which $R^1$ and $R^2$ are alkyl groups which may be the same or different.

"Tri-(Normal Alkyl)aluminum" is a compound having the formula $(R^1)(R^2)(R^3)Al$, where $R^1$, $R^2$ and $R^3$ are linear alkyl groups which may be the same or different.

"Tri-(Beta-Branched Alkyl)aluminum" is a compound having the formula $(R^1)(R^2)(R^3)Al$, where $R^1$, $R^2$ and $R^3$ are alkyl groups which are branched at the beta carbon atom and which may be the same or different.

Background

Tri-(beta-branched alkyl)aluminum compounds are useful as reducing agents in a variety of organic reactions, and as a raw material for production of alcohols by controlled oxidation followed by hydrolysis. However, it has been known at least since the days of Ziegler that production of tri-(beta-branched alkyl)aluminum compounds can be extremely difficult, even in low yield percentages, since tri-(beta-branched alkyl)aluminum compounds are much more reactive, i.e., much less stable, than trialkylaluminum compounds having alkyl groups which are linear or have one or more branches more remote than the beta carbon atom.

Accordingly, a novel, highly efficient and economical process to enable commercial production of tri-(beta-branched alkyl)aluminum compounds would constitute a useful contribution to the art. Likewise, a process which permits the reutilization of these compounds would be highly beneficial. The subject invention is deemed to make such contributions to the art.

SUMMARY OF THE INVENTION

A novel and highly efficient process for the production of tri-beta-branched alkyl aluminum compounds from linear olefin is provided by this invention. The process permits production of tri-(beta-branched alkyl)aluminum compounds in high yield (over 85 mol %) and in the same reaction vessel, if so desired. This process comprises:

a) dimerizing one or more vinylolefin monomers with an alkyl aluminum catalyst to form a first product mixture comprising at least vinylolefin monomer, trialkylaluminum in which each alkyl group has the same number of carbon atoms and skeletal structure as the vinylolefin monomer, and vinylidene olefin, b) removing the vinylolefin monomer from the first product mixture while concurrently converting the trialkylaluminum and the vinylidene olefin to tri-(beta-branched alkyl)-aluminum by reactive distillation to form a second product mixture comprising at least tri-(beta-branched alkyl) aluminum, and c) distilling the second product mixture to purify the tri-(beta-branched alkyl)aluminum.

In a particularly preferred embodiment of the invention, the vinylolefin monomer of this process is vinylolefin having n carbon atoms, where n is an integer in the range of from 3 to about 24, the alkyl aluminum catalyst is initially triethylaluminum, the dimerization is conducted at a temperature in the range of about 100° to about 250° C., and the reactive distillation is conducted at a temperature in the range of about 150° to about 250° C.

This invention also provides a process for the production of at least one tri-(beta-branched alkyl)aluminum from a first product mixture comprising at least one vinylolefin monomer, at least one trialkylaluminum in which each alkyl group has the same number of carbon atoms and skeletal structure as the vinylolefin monomer, and at least one vinyl olefin. The process comprises removing the vinylolefin monomer from the first mixture while concurrently converting the trialkylaluminum and the vinylidene olefin to tri-(beta-branched alkyl)aluminum by reactive distillation to form a second product mixture comprising at least one tri-(beta-branched alkyl)aluminum. In a particularly preferred embodiment, the vinylolefin monomer of this process is vinylolefin having n carbon atoms, where n is an integer in the range of from 3 to about 24, and said reactive distillation is conducted at a temperature in the range of about 120° to about 300° C.

In addition, this invention provides an improvement in processes for the production of tri-(beta branched alkyl) aluminum, the improvement comprising:

a) dimerizing one or more vinylolefin monomers with an alkyl aluminum catalyst to form a first product mixture comprising at least (i) vinylolefin monomer, (ii) trialkylaluminum in which each alkyl group has the same number of carbon atoms and skeletal structure as said vinylolefin monomer, and (iii) vinylidene olefin, b) removing said vinylolefin monomer from said first product mixture while concurrently converting said trialkylaluminum and said vinylidene olefin to tri-(beta-branched alkyl)-aluminum by reactive distillation to form a second product mixture comprising at least tri-(beta-branched alkyl)aluminum and vinylidene olefin, c) distilling said second product mixture to purify said tri-(beta-branched alkyl)aluminum and to remove said vinylidene olefin, and d) recycling at least a portion of said tri-(beta-branched alkyl)aluminum as catalyst for step a) hereof.

The process of this invention requires only a relatively small amount of process equipment in that all of the operations can be conducted in the same reaction vessel. For example, each of the process steps may be conducted in a single reactor, such as a glass-lined reactor equipped with suitable distillation auxiliaries. If the process uses a single vinylolefin in the initial dimerization reaction, the distillation equipment can be very simple in design and construction because the separations in which it is used will not contain materials having close boiling points. For example if 1-octene is dimerized using trioctylaluminum catalyst, the olefins in the system are primarily $C_8$ and $C_{16}$ olefins, which are readily separated by distillation. Thus, in another particularly preferred embodiment, all of the process steps of this invention are carried out within the same reactor.

The above and other embodiments of this invention will become still further apparent from the ensuing description and appended claims.

Further Detailed Description of the Invention

As previously stated, one of the embodiments of this invention provides a three-step process for the production of tri-(beta-branched alkyl)aluminum in high yield. Each of these steps (dimerization, reactive distillation, and purification) will now be discussed in greater detail.

Dimerization

The vinylolefin monomers which are subjected to dimerization in the process of this invention typically have at least 3 and preferably at least 4 carbon atoms per molecule and can be individual olefins or mixtures of two or more such olefins. Preferred vinylolefins are linear (i.e., straight chain) vinylolefins typified by such compounds as propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, and analogous higher homologs which may contain up to about 36 carbon atoms, but more preferably, no more than about 24 carbon atoms, and still more preferably no more than about 18 carbon atoms. Linear vinylolefins having in the range of 4 to about 14 carbon atoms per molecule and mixtures of any two or more such olefins are particularly preferred. Less preferred are branched vinylolefins. Examples include such compounds as 4-methyl-1-pentene, 4-methyl-1-hexene, 5-methyl-1-hexene, 4,5-dimethyl-1-hexene, 5,5-dimethyl-1-hexene, 4-ethyl-1-hexene, 4-methyl-1-heptene, 5-methyl-1-heptene, 6-methyl-1-heptene, 5,5-dimethyl-1-heptene, 4,6-dimethyl-1-heptene, and similar branched higher homologs which likewise may contain up to about 36 carbon atoms, but more preferably, no more than about 24 carbon atoms, and still more preferably no more than about 18 carbon atoms. It will be understood and appreciated that the vinylolefins which are dimerized in the process can be a mixture of linear and branched vinylolefins. Likewise, the vinylolefins used can be in admixture with other hydrocarbons such as paraffinic, cycloparaffinic, and/or aromatic hydrocarbons. Where the vinylolefin monomer of this invention is a mixture of different olefins, it is preferred that the mixture be composed of two different vinylolefins, one vinylolefin having no fewer that 3 carbon atoms, and the other having no fewer than 4 carbon atoms, such that the difference between their respective carbon numbers equals 1 or 2.

The alkyl aluminum dimerization catalyst is typically one or more trialkyl aluminum compounds in which each alkyl group contains at least two carbon atoms. Examples of such compounds include triethylaluminum, tripropylaluminum, tributylaluminum, tripentyl-aluminum, trihexylaluminum, tri(4-methylpentyl)aluminum, triheptylaluminum, trioctylaluminum, tri(4-methylheptyl)aluminum, tri(5-methylheptyl)aluminum, tri(6-methylheptyl)-aluminum, tridecylaluminum, tri(4-ethyloctyl)aluminum, tri(6-ethyloctyl)-aluminum, tri(6,6-dimethyloctyl)aluminum, tris(dodecyl) aluminum, tris(tetradecyl)aluminum, and the like, including mixtures of compounds of this type. Dialkylaluminum hydrides having at least two carbon atoms in each alkyl group may also be charged as the catalyst, and may in fact react with an vinylolefin monomer to form trialkylaluminum in situ.

The dimerization conditions of this invention include use of substantially anhydrous feed materials and reaction conditions, and use of temperatures in the range of about 100° to about 250° C., preferably in the range of about 140° to about 200° C. The proportions of the aluminum alkyl catalyst relative to the olefin being dimerized can be varied over a considerable range. Thus the aluminum alkyl catalyst will typically be used in amounts in the range of about 0.001 to about 1.0 mol (preferably in the range of about 0.01 to about 0.17 mol; most preferably in the range of about 0.06 to about 0.17) per mol of vinylolefin monomer starting material. The reaction is relatively slow at the lower reaction temperatures and lower aluminum alkyl catalyst concentrations, while at higher temperatures and higher aluminum alkyl catalyst concentrations, the reaction rate is faster. Thus, the reaction should be conducted for a period of time sufficient under the conditions employed to dimerize at least about 70 percent (preferably at least 90 percent) of the initial vinylolefin monomer into other products.

Reactive Distillation

Upon completion of the aforesaid dimerization, a first product mixture is produced which comprises at least one vinylolefin monomer, at least one trialkylaluminum in which each alkyl group has the same number of carbon atoms and skeletal structure as the vinylolefin monomer, and at least one vinylidene olefin. The vinylolefin monomer is as described above. While it is preferred that the trialkylaluminum compound be a tri-(normal alkyl)aluminum compound, the alkyl groups of the trialkylaluminum compound may be either linear or branched (other than at the beta carbon atom), depending upon the vinylolefin monomer structure. Examples of such compounds include tripropylaluminum, tributylaluminum, tripentylaluminum, trihexyl-aluminum, triheptylaluminum, trioctylaluminum, trinonylaluminum, tridecylaluminum, tris(dodecyl) aluminum, tris(tetradecyl)aluminum, and the like, including higher homologs and mixtures of compounds of this type. Dialkylaluminum hydrides having at least three carbon atoms in each alkyl group may also be present, and may in fact react with vinylolefin to form trialkylaluminum in situ.

The vinylidene olefin will typically have at least 6 carbon atoms, and may exist as a single form of olefin or as a mixture of different vinylidene olefins. Examples of such compounds include 2-methyl-1-pentene, 2-ethyl-1-hexene, 2-propyl-1-heptene, 2-butyl-1-octene, 2-pentyl-1-nonene, 2-hexyl-1-decene, 2-heptyl-1-undecene, 2-octyl-1-dodecene, 2-nonyl-1-tridecene, 2-decyl-1-tetradecene, 2-undecyl-1-pentadecene, 2-dodecyl-1-hexadecene, 2-hexyl-1-nonene, 2-pentyl-1-decene, and higher homologs, including mixtures of such compounds.

Although the stability of trialkylaluminum, in which the alkyl groups are linear or have one or more branches more remote than the beta carbon atom, is several times greater than tri-(beta-branched alkyl)aluminum, in conducting the reactive distillation a shift in this equilibrium is effected by removal of vinylolefin monomer from the first product mixture. Thus a key feature of this reaction is the shifting of the equilibrium by means of reactive distillation under reactive distillation conditions. Such conditions include maintaining substantially anhydrous reaction conditions, and a temperature in the range of about 120° to about 300° C. (preferably in the range of about 150° to about 250° C.). The reactive distillation should be conducted for a period of time sufficient under the conditions employed to convert at least about 70 percent (preferably at least 85 percent) of the trialkylaluminum into tri-(beta-branched alkyl)aluminum.

Purification

Upon completion of reactive distillation, a second product mixture is produced which comprises at least one tri-(beta-branched alkyl)aluminum. The tri-(beta-branched alkyl)-aluminum compound is typically one or more trialkylaluminum compounds in which each alkyl group contains at least six carbon atoms and is branched at the beta carbon atom. When the starting vinylolefin monomer has a particular number of carbon atoms, the tri-(beta-branched alkyl)

aluminum compound has the formula $AlR_3$, where R is an alkyl group branched at the beta carbon atom and having n carbon atoms where n is an even number in the range of 6 to about 48 carbon atoms (preferably about 12 to about 24 carbon atoms), the branch on the beta carbon atom having (n/2)-2 carbon atoms. When the starting vinylolefin monomer is comprised of a mixture of two vinylolefins, one having x carbon atoms, and the other having y carbon atoms and x is greater than y, R is an alkyl group branched at least at the beta carbon atom and has x+y carbon atoms, where x+y is an integer in the range of 6 to about 48 carbon atoms (preferably about 12 to about 24 carbon atoms), the branch on the beta carbon atom having y or y-2 carbon atoms. Examples of such compounds include tri(2-methylpentyl)-aluminum, tri(2-ethylhexyl)aluminum, tri(2-propylheptyl) aluminum, tri(2-butyloctyl)aluminum, tri(2-pentyl-nonyl) aluminum, tri(2-hexyl-decyl)aluminum, tri(2-heptylundecyl)aluminum, tri(2-octyldodecyl)-aluminum, tri(2-nonyltridecyl)aluminum, tri(2-decylbutadecyl)-aluminum, and their higher homologs, including mixtures of such compounds. Other examples of such compounds include tri(2-isopropyl-5-methylhexyl)aluminum, tri(2-isobutyl-6-methylheptyl)-aluminum, tri(2-isobutyl-4-methylpentyl)aluminum, tri[2-isopropyl-6-methylheptyl) aluminum, tri(2-(4-methylpentyl)octyl]aluminum, tri(2-isobutyldecyl)aluminum, and their higher homologs, including mixtures of such compounds. It is preferred that the alkyl groups of the compound branch only at the beta carbon atom, and that the branch itself is linear. Dialkylaluminum hydrides having at least six carbon atoms in each alkyl group may also be produced, and may in fact react with a vinylidene monomer to form tri(beta-branched alkyl) aluminum in situ.

Purification of the tri-(beta-branched alkyl)aluminum may be carried out by distillation under substantially anhydrous, distillation conditions which include a temperature in the range of about 100° to about 300° C.

In another embodiment of this invention, an improvement in the production of tri-(beta-branched alkyl)aluminum requires the additional step of recycling the tri-(beta branched alkyl)aluminum produced in accordance with this invention as catalyst for the dimerization step of this invention. In this improved process, the second product mixture formed in the reactive distillation step of this invention comprises at least tri-(beta-branched alkyl)aluminum and vinylidene olefin. In the subsequent purification by distillation, the vinylidene olefin is removed while the tri-(beta-branched alkyl)aluminum is purified. At least a portion of the purified tri-(beta-branched alkyl)aluminum is then recycled as catalyst for dimerization.

It will be understood that the process of this invention may be conducted continuously, semi-continuously, or in batch operations. Of these methods, it is preferred to operate on a batch basis as this provides the greatest cost-effectiveness.

The following examples serve to illustrate this invention, but do not limit it. All parts are by weight unless otherwise indicated.

EXAMPLE 1

A total of 140 pounds (about 63.5 kg) of 1-hexene are dimerized using 3.2 pounds (about 1.5 kg) of triethylaluminum. The reaction is conducted by charging the 1-hexene and triethylaluminum to a glass-lined reactor at room temperature, maintained under a nitrogen blanket, equipped with a stirrer, and configured for total reflux of condensate. Over a two-hour period the stirred mixture is heated from room temperature up to 125° C. Thereafter the stirred reaction mixture is kept at 125°–128° C. for 113 hours. The reaction mixture then was distilled at a temperature of 165°–168° C. and at a pressure of 300 mmHg for 1 hour to remove $C_6$ and $C_8$ olefins and shift the equilibrium of the mixture toward production of tri-(2-butyloctyl)aluminum.

The temperature of the same reactor was then reduced to 120° C., and pressure was reduced to 5 mmHg. These conditions were maintained for 1 hour to purify the resulting tri-(2-butyloctyl)aluminum by removing dimerized $C_{12}$ olefin from the reaction product. Table 1 below summarizes results of a reaction conducted in this manner. It will be noted that, in the tables set forth hereafter, "Vi" is vinylolefin, "2 Int" is an olefin in which the double bond is between the second and third carbon atom, "3+ Int" is an olefin in which the double bond is between two carbon atoms each of which is at least the third carbon atom away from either end of the chain, "Vd" is vinylidene olefin, "Al" is aluminum, and $alR=⅓(AlR_3)$.

TABLE 1

|  | Initial Feed | Dimerization Product (after 113 hrs) | Reactive Distillation Product (1 hr) | Purification Product (1 hr) |
|---|---|---|---|---|
| $C_6$ GC area % (hydrolyzed) | 99.9 | 16.2 | 1.9 | 3 |
| $C_8$ GC area % (hydrolyzed) | 0.1 | 6.2 | 1.4 | 0.3 |
| $C_{12}$ GC area % (hydrolyzed) | — | 75.4 | 94 | 85.8 |
| Vi mol % in olefin (hydrolyzed) | 98 | 15.7 | — | — |
| 2 Int mol % in olefin (hydrolyzed) | 0.3 | 1.9 | — | 2.4 |
| 3 + Int mol % in olefin (hydrolyzed) | — | 4 | 5.5 | 13.1 |
| Vd mol % in olefin (hydrolyzed) | 1.7 | 78.4 | 94.5 | 84.5 |
| Feed Mol Ratio of alR to Vi | 0.05 | — | — | — |
| Al (ppm) | 5680 | 6050 | 8050 | 46300 |

In addition, NMR analysis of the unhydrolyzed purification product indicated 88.9 mol % alR (where $alR=⅓×AlR_3$). From this example it can be seen that exceptionally high yields of tri-(beta-branched alkyl)aluminum are possible with a minimum amount of equipment using the processes of this invention.

EXAMPLE 2

A total of 94 pounds (about 42.6 kg) of 1-hexene and 72 pounds (about 32.7 kg) of 1-octene are dimerized using 13.4 pounds (about 6.1 kg) of tri-(beta-branched alkyl)aluminum produced in the reaction of Example 1. The reaction is conducted by charging the mixture of 1-hexene and 1-octene and the tri-(beta-branched alkyl)aluminum to a glass-lined reactor at room temperature, maintained under a nitrogen blanket, equipped with a stirrer, and configured for total reflux of condensate. Over a two-hour period the stirred mixture is heated from room temperature up to 120° C. Thereafter the stirred reaction mixture is kept at 120° C. for 51 hours. The temperature is then raised to 142° C. and the stirred reaction mixture is maintained at this temperature for an additional 69 hours. Table 2 below summarizes results of a reaction conducted in this manner.

TABLE 2

|  | Initial Feed | Dimerization Product (after 19 hrs) | Dimerization Product (after 51 hrs) | Dimerization Product (after 90 hrs) | Dimerization Product (after 120 hrs) |
|---|---|---|---|---|---|
| $C_6$ GC area % (hydrolyzed) | 53.8 | 46.4 | 35.1 | 13.4 | 7.3 |
| $C_8$ GC area % (hydrolyzed) | 41.2 | 34.3 | 24.7 | 9.2 | 5.7 |
| $C_{12}$ GC area % (hydrolyzed) | 4.5 | 10.5 | 17.3 | 30.2 | 33.8 |
| $C_{14}$ GC area % (hydrolyzed) | — | 5.9 | 16.0 | 34.1 | 38.6 |
| $C_{16}$ GC area % (hydrolyzed) | — | 2.7 | 6.3 | 12.7 | 13.3 |
| Vi mol % in olefin (hydrolyzed) | 96.3 | 84.3 | 66.8 | 23.5 | 10.5 |
| 2 Int mol % in olefin (hydrolyzed) | 0.8 | 1.5 | 2.4 | 4.4 | 5.9 |
| 3 + Int mol % in olefin (hydrolyzed) | — | 0.9 | 1.4 | 4.2 | 5.3 |
| Vd mol % in olefin (hydrolyzed) | 2.6 | 13.3 | 29.2 | 67.9 | 78.3 |
| Feed Mol Ratio of alR to Vi | 0.03 | — | — | — | — |
| Al (ppm) | 3460 | 3520 | 3430 | 3200 | 3580 |

Clearly, the recycled tri-beta-branched alkylaluminum is highly effective as the alkyl aluminum catalyst used in the dimerization step of the process of this invention.

It is to be clearly understood and appreciated that in the specification and claims hereof all references to substances used in the process relate to the initial identity of the material being used and such references do not in any way require that during the process the substances must maintain that identity until the instant, if any, that a chemical transformation occurs to form a different substance. In short, once two or more of the identified materials are brought into contact with or proximity to each other, whether under reaction conditions or not, one or more of them may undergo a change in identity as compared to their original identity, and such change or changes are encompassed by the claims hereof as long as the end results of the overall process are as described herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the production of at least one tri-(beta-branched alkyl)aluminum which comprises:
    a) dimerizing one or more vinylolefin monomers with an alkyl aluminum catalyst to form a first product mixture comprising at least vinylolefin monomer, trialkylaluminum in which each alkyl group has the number of carbon atoms and skeletal structure as said vinylolefin monomer, and vinylidene olefin,
    b) removing said vinylolefin monomer from said first product mixture while concurrently converting said trialkylaluminum and said vinylidene olefin to tri-(beta-branched alkyl)aluminum by reactive distillation to form a second product mixture comprising at least tri-(beta-branched alkyl)aluminum, and
    c) distilling said second product mixture to purify said tri-(beta-branched alkyl)aluminum..

2. A process according to claim 1 wherein said vinylolefin monomer has n carbon atoms, where n is an integer in the range of from 3 to about 24.

3. A process according to claim 1 wherein said vinylolefin monomer is a mixture comprising at least two vinylolefins, one of which has n carbon atoms and another of which has n+1 or n+2 carbon atoms, where n is an integer in the range of from 3 to about 24.

4. A process according to claim 1 wherein said alkyl aluminum catalyst is at least one linear alkyl aluminum catalyst.

5. A process according to claim 1 wherein said alkyl aluminum catalyst is initially triethylaluminum.

6. A process according to claim 1 wherein said dimerization is conducted at a temperature in the range of about 100° to about 250° C.

7. A process according to claim 1 wherein said reactive distillation is conducted at a temperature in the range of about 120° to about 300° C.

8. A process according to claim 1 wherein said process is entirely conducted within a single reaction vessel.

9. A process according to claim 1 wherein said vinylolefin monomer has n carbon atoms, where n is an integer in the range of from 3 to about 24, said alkyl aluminum catalyst is initially triethylaluminum, said dimerization is conducted at a temperature in the range of about 100° to about 250° C., and said reactive distillation is conducted at a temperature in the range of about 150° to about 250° C.

10. A process according to claim 1 wherein the mol ratio of said alkyl aluminum catalyst to said vinylolefin monomer is in the range of about 0.01 to about 0.17.

11. A process according to claim 1 wherein the mol ratio of said alkyl aluminum catalyst to said vinylolefin monomer is in the range of about 0.06 to about 0.17.

12. A process for the production of at least one tri-(beta-branched alkyl)aluminum from a first product mixture comprising at least one vinylolefin monomer, at least one tri-alkylaluminum in which each alkyl group has the number of carbon atoms and skeletal structure as said vinylolefin monomer, and at least one vinylidene olefin, said process comprising removing said vinylolefin monomer from said first mixture while concurrently convening said trialkylaluminum and said vinylidene olefin to tri-(beta-branched alkyl)aluminum by reactive distillation to form a second product mixture comprising at least one tri-(beta-branched alkyl)aluminum.

13. A process according to claim 12 wherein said vinylolefin monomer has n carbon atoms, where n is an integer in the range of from 3 to about 24.

14. A process according to claim 12 wherein said vinylolefin monomer is a mixture comprising at least two vinylolefins, one of which has n carbon atoms and another of which has n+1 or n+2 carbon atoms, where n is an integer in the range of from 3 to about 24.

15. A process according to claim 12 wherein said reactive distillation is conducted at a temperature in the range of about 120° to about 300° C.

16. A process according to claim 12 wherein said process is entirely conducted within a single reaction vessel.

17. A process according to claim 12 wherein said vinylolefin monomer has n carbon atoms, where n is an integer in the range of from 3 to about 24, and said reactive distillation is conducted at a temperature in the range of about 120° to about 300° C.

18. In a process for production of tri-(beta branched alkyl)aluminum, the improvement which comprises:

a) dimerizing one or more vinylolefin monomers with an alkyl aluminum catalyst to form a first product mixture comprising at least (i) vinylolefin monomer, (ii) trialkylaluminum in which each alkyl group has the same number of carbon atoms and skeletal structure as said vinylolefin monomer, and (iii) vinylidene olefin, b) removing said vinylolefin monomer from said first product mixture while concurrently converting said trialkylaluminum and said vinylidene olefin to tri-(beta-branched alkyl)aluminum by reactive distillation to form a second product mixture comprising at least tri-(beta-branched alkyl)aluminum and vinylidene olefin, c) distilling said second product mixture to purify said tri-(beta-branched alkyl)aluminum and to remove said vinylidene olefin, and d) recycling at least a portion of said tri-(beta-branched alkyl)aluminum as catalyst for step a) hereof.

19. A process according to claim 18 wherein said vinylolefin monomer has n carbon atoms, where n is an integer in the range of from 3 to about 24.

20. A process according to claim 18 wherein said vinylolefin monomer is a mixture comprising at least two vinylolefins, one of which has n carbon atoms and another of which has n+1 or n+2 carbon atoms, where n is an integer in the range of from 3 to about 24.

21. A process according to claim 18 wherein said alkyl aluminum catalyst is initially at least one linear alkyl aluminum catalyst.

22. A process according to claim 18 wherein said alkyl aluminum catalyst is initially triethylaluminum.

23. A process according to claim 18 wherein said dimerization is conducted at a temperature in the range of about 100° to about 250° C.

24. A process according to claim 18 wherein said reactive distillation is conducted at a temperature in the range of about 120° to about 300° C.

25. A process according to claim 18 wherein said process is entirely conducted within a single reaction vessel.

26. A process according to claim 18 wherein said vinylolefin monomer has n carbon atoms, where n is an integer in the range of from 3 to about 24, said alkyl aluminum catalyst is initially triethylaluminum, said dimerization is conducted at a temperature in the range of about 100° to about 250° C., and said reactive distillation is conducted at a temperature in the range of about 150° to about 250° C.

* * * * *